US005795159A

United States Patent [19]
Ralls et al.

[11] Patent Number: 5,795,159
[45] Date of Patent: Aug. 18, 1998

[54] MERCURY REMOVAL METHOD AND APPARATUS

[75] Inventors: Stephen Alden Ralls, Great Lakes; William Corry Roddy, Grayslake, both of Ill.

[73] Assignee: The United States of America as represented by the Secretary of the Navy, Washington, D.C.

[21] Appl. No.: 595,689

[22] Filed: Feb. 2, 1996

[51] Int. Cl.[6] ............................................ A61C 17/04
[52] U.S. Cl. ............................ 433/92; 604/319; 210/295
[58] Field of Search ............................ 433/91, 92, 95; 210/294, 295, 299, 532.1; 604/319–321

[56] References Cited

U.S. PATENT DOCUMENTS

| 4,385,891 | 5/1983 | Ligotti | 433/92 |
| 5,055,198 | 10/1991 | Shettigar | 604/319 |
| 5,087,250 | 2/1992 | Lichte et al. | 604/319 |
| 5,354,468 | 10/1994 | Richards | 433/92 |

FOREIGN PATENT DOCUMENTS

| 0284641 | 10/1988 | European Pat. Off. | 433/92 |
| 3231272 | 2/1984 | Germany | 433/92 |
| 3423836 | 1/1986 | Germany | 433/92 |
| 8302720 | 8/1983 | WIPO | 433/92 |

Primary Examiner—Ralph A. Lewis
Attorney, Agent, or Firm—Edward Saul; A. D. Spevack

[57] ABSTRACT

A method and apparatus to treat dental waste water has been developed in which a slurry of water and solid waste particles, including mercury-containing amalgam and soluble and suspended mercury and other heavy metals, is collected under vacuum into an main chamber. The particulate-containing liquid slurry settles into a main chamber and into the central collection well of a removable filter while the vacuumed air exits the main chamber and continues toward a vacuum source. The liquid slurry is drawn by vacuum through a removable filter making the effluent substantially free of mercury-containing particulate material. The resulting filtered effluent is ready for further treatment of soluble and suspended mercury, if necessary, before being conveyed into a public sewer system. When a certain level of particulate material has been collected, the removable filter can be sealed and the particulate contents disposed or reclaimed.

2 Claims, 2 Drawing Sheets

MERCURY REMOVAL METHOD AND APPARATUS

BACKGROUND OF THE INVENTION

1. Field of the Invention

This invention relates to a simple method and apparatus for removing particulate material containing mercury, silver and other metals from dental waste water providing a filtered effluent suitable for discharge into a public sewer system or, if necessary, for further treatment of soluble and suspended mercury.

2. Description of the Prior Art

Dental amalgam is a common dental restorative material which normally contains mercury, silver, zinc, copper and tin, and occasionally other metals. During the most commonly performed dental procedures, dental amalgam is removed as waste material from the patient's mouth. Removal of the amalgam from the patient's mouth typically takes place by vacuum extraction as part of a rinsing liquid, such as water. The mercury removed is from the dental amalgam and is in the form of mercury-containing particulate material and the soluble and suspended mercury-containing fraction. Other material such as pieces of teeth, particles of dental cements or bases, pieces of restorative materials, etc. are also removed with the dental amalgam and rinsing liquid to form a liquid waste water slurry. Within this invention, the term particulate material includes, but is not limited to, matter, debris, compounds, mixtures, suspensions or similar which have particulate components or characteristics.

Mercury is generally classified as a toxic material which requires special handling and disposal procedures. Since the dental amalgam contains mercury, a need exists to simply, easily, efficiently and effectively remove the mercury-containing particulate material from the waste water slurry removed by vacuum from the patient's mouth prior to eventual discharge of the treated waste water into the public sewer system. A need also exists to simply, easily, efficiently and effectively produce a filtered effluent which is suitable for discharge into a public sewer system or further treatment, if necessary, of the soluble and suspended mercury-containing fraction of the waste water slurry. A further need exists to provide a means to simply, easily, efficiently and effectively collect, seal and store the particulate waste material containing mercury, silver and other metals which can then be disposed of or reclaimed.

Though not appreciably related to the invention described herein, there have been several efforts of peripheral interest. While some similarity of purpose is noted in these efforts and while such apparatus described may be satisfactory for the collection of some particulate material under certain conditions, such apparatus differs considerably in function, design, operation and features from the invention described herein. Apparatus previously has been disclosed, such as in U.S. Pat. Nos. 3,777,403 to Ritchie and 4,385,891 to Ligotti which use different containers through which the mixture of liquid and solids are passed and the solids settle out under the force of gravity. Neither apparatus uses a sealable, removable filter with a central collection well for collecting particulate material and a vacuum is not used to assist slurry flow through a removable filter. Both are designed to primarily separate larger particles of precious metal for reclamation.

Ludvigsson et al. U.S. Pat. No. 5,205,743 disclosed a system in which the waste material is collected in a suction stream and passed through a series of filters, the last being preferably a selenium filter. This apparatus does not use a sealable, removable filter with a central collection well for collecting particulate material and a vacuum is not used to assist slurry flow through a removable filter. Bishop U.S. Pat. No. 3,138,873 described a suction system which passes a liquid slurry of the waste material through a porous bag which traps and collects the solid particles and passes the liquid. This apparatus must have a compromise as to the size of the particles collected and the liquid flow rate as determined by the porosity of the bag.

In Meyer's U.S. Pat. No. 5,017,135, particles are separated from the waste liquid as it is drawn under suction force in a sharply turning path past a series of traps into which particles settle out under force of gravity. No filtering is performed and there is no specific provision for collection of small particles or soluble mercury. Sundström U.S. Pat. No. 5,114,578 passes a slurry of water, saliva and particles through a pre-settling tank, into which the larger particles settle, and then in an upward inclined path through a special filter formed by a bundle of plastic tubes. In using this arrangement it is difficult to collect and dispose of the smaller metal particles collected on the walls of the filter and filter plastic tubes.

Ralls et al. in a pending U.S. patent application Ser. No. 08/566,391 filed 1 Dec. 1995, address a problem similar to that addressed with the invention described herein, however, their method and system are substantially different. Their system is based primarily on the time-related sedimentation of dental waste water wherein the accumulated waste water is allowed to settle, usually overnight, then by using a series of valves and aided by a sight glass, a portion of the waste water is decanted, filtered and additionally treated with co-polymers, ion exchange media or similar.

SUMMARY OF THE INVENTION

Accordingly, an object of this invention is to provide a method and apparatus to simply, easily, efficiently and effectively remove particulate material containing mercury, silver and other metals from the waste water slurry produced as a result of certain types of dental procedures. This object is accomplished by use of the following: a vacuum source to supply the apparatus with the waste water slurry; a slurry gravity trap to separate the liquid slurry from the vacuumed air; vacuum-assisted filtering of the slurry; a removable and sealable filter; and a collection well within the removable filter that retains particulate material for storage, reclamation or disposal.

An additional object of this invention is to provide a method and apparatus to simply, easily, efficiently and effectively provide a dental waste water effluent suitable for discharge into a public sewer system or for further treatment, if necessary, to remove soluble and suspended mercury by additional filtering or treatment with co-polymers, co-precipitants, ion scavengers, ion exchange media or other suitable methods.

An additional object of this invention is to provide a method and apparatus to simply, easily, efficiently and effectively collect, seal and store the particulate dental waste material containing mercury, silver and other metals which can then be disposed of or reclaimed. A sealable removable filter with a central collection well is used to accomplish this object.

BRIEF DESCRIPTION OF THE DRAWING

A more complete appreciation of the invention will be readily obtained by reference to the following Description of the Preferred Embodiments and the accompanying drawing in which like numerals in different figures represent the same structures or elements. The representations in each of the figures is diagrammatic and no attempt is made to indicate actual scales or precise ratios. Proportional relationships are shown as approximations.

DESCRIPTION OF THE PREFERRED EMBODIMENTS

Figure 1:
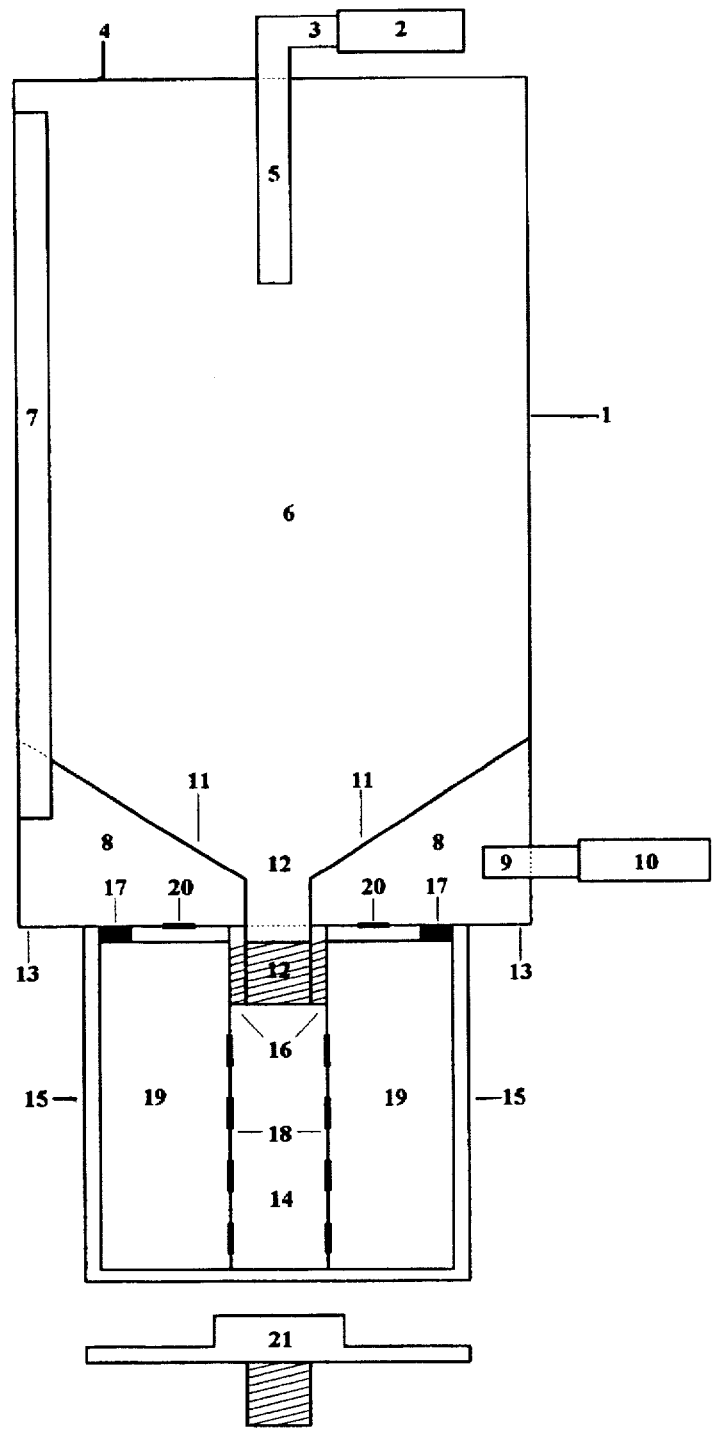
FIG. 1 is an embodiment of the apparatus from a side view including a side view of the filter cover.
Figure 2:
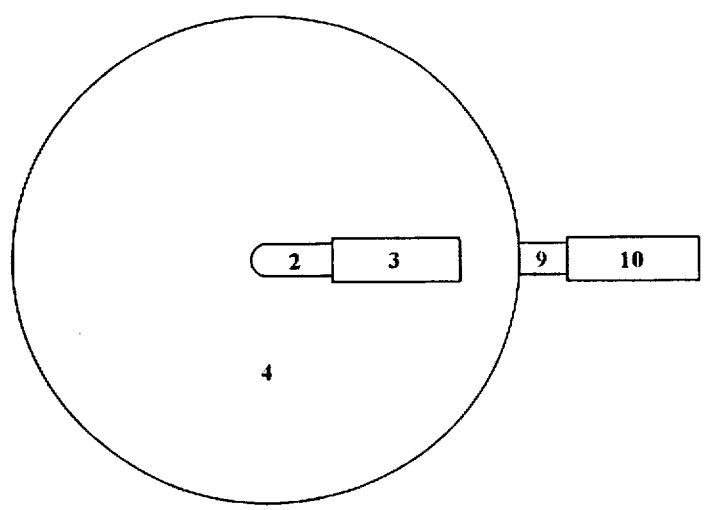
FIG. 2 is an embodiment of the apparatus from a top view.
Figure 3:
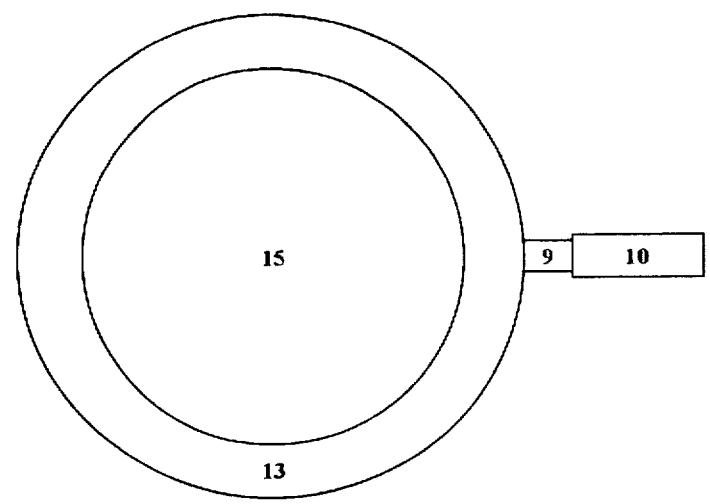
FIG. 3 is an embodiment of the apparatus from a bottom view.

Referring to FIGS. 1, 2 and 3, a preferred embodiment includes a cylindrically shaped housing 1 to encase the apparatus. Waste material produced during a dental procedure is normally removed from the patient's mouth through an input vacuum line 2 under suction produced by a vacuum source (not shown), e.g., vacuum turbines. The waste material is in liquid slurry form and includes liquid components such as rinse water, saliva and blood and solid material such as pieces of teeth, particles of dental cement or bases, and pieces of restorative materials such as new and previously placed, mercury-containing amalgam restorations. The mercury can be in the form of relatively large pieces, and smaller insoluble and soluble particles entrained in the waste water slurry.

The input vacuum line 2 serving a dental operatory (or a plurality of operatories) attaches to an input vacuum connection 3 in the flat (or slightly rounded) top 4 of the apparatus housing 1. The input vacuum connection 3 extends by an input vacuum connection tube 5 into the main chamber 6. The main chamber 6 is connected by a chamber connection tube 7 to the output chamber 8. The vacuumed air passes from the main chamber 6 through the chamber connection tube 7 to the output chamber 8, out the vacuum output connection 9, through the vacuum source line 10 to the vacuum source (not shown). As a vacuum is applied from a suitable source to the output chamber 8 via the vacuum source line 10 and the vacuum output connection 9, a vacuum is simultaneously created in the main chamber 6 through the chamber connection tube 7 and exerted on the input vacuum connection tube 5, through the input vacuum connection 3 to the input vacuum line 2 which serves the dental operatory and patient (not shown). The waste water slurry removed by vacuum from the patient is trapped by gravity in the lower most aspects of the main chamber 6 and directed through an inferior opening in an interior funnel 11, through a male-threaded hollow tube 12, through a round, flat base 13 of the housing 1 and into a central collection well 14 of a cylindrically shaped, removable filter device 15. In this manner, the waste water slurry is directed from the main chamber 6 to a central collection well 14 of a removable filter device 15.

The removable filter device 15 is attached to the base 13 of the housing 1 by a female-threaded filter device opening 16 which screws onto a male-threaded hollow tube 12 whose unthreaded portion is attached to the inferior opening of the interior funnel 11 and whose threaded portion protrudes inferiorly through the base 13 of the housing 1. The removable filter device 15 can then be screwed onto the male threads of the hollow tube 12 protruding through the base 13 of the housing 1 and sealed by a rubber (or similar material) gasket ring 17 which seals with the base 13 of the housing 1 as the filter device 15 is tightened. The cylindrical wall 18 of the central collection well 14 is perforated and leads to peripherally placed filter media 19 positioned between the perforated cylindrical wall 18 and the exterior surface of the removable filter device 15. As a vacuum is exerted in the output chamber 8, the liquid slurry is drawn through the filter media 19 resulting in a filtered effluent. The filtered effluent is drawn through perforations 20 normally arranged circularly on the base 13 of the housing 1 and into an output chamber 8. The filtered effluent which collects in the output chamber 8 is removed under vacuum through a vacuum output connection 9, through a vacuum source line 10, toward the vacuum source (not shown) and ultimately discharged into a public sewer system. The filtered effluent can be further treated, if necessary, to remove soluble and suspended mercury. The filter device 15 can be removed when a certain level of particulate material has been collected and sealed with a filter cover with a centrally located male-threaded plug 21. The filter cover with a centrally located male-threaded plug 21 consists of a usually round, flat or nearly flat cover with a knob on one side which permits the male-threaded plug on the other side to be screwed into the female threads of the filter device opening 16 thereby creating a seal with the rubber gasket ring 17. The edge of the filter cover extends outwardly to cover the rubber gasket ring of the filter device 15 and can extend over and slightly down the sides of the filter device 15 forming a lip. The removable filter device 15 is constructed in such a way as to permit easy access, when unsealed, to the central collection well 14 which retains larger particulate material containing mercury, silver and other metals; access is typically through the female-threaded filter device opening 16. The removable filter device 15 is also constructed in such a way as to permit disassembly to permit access to the filter media 19 and other interior spaces of the filter device 15 that retain smaller-sized particulate material containing mercury, silver and other metals.

The components of the invention are made of any suitable material. Various fixtures, fittings and internal tubes and plumbing can be made of PVC, CPVC, ABC, stainless steel, brass, copper, plastic, fiberglass, polypropylene, polyethylene or other suitable, usually rigid material. The external tubing and connection components are also of brass, stainless steel, copper, plastic, PVC, CPVC, ABC, fiberglass, polypropylene, polyethylene, rubber or equivalent material and can be either flexible or rigid. The housing, the top and base of the housing and internal chamber walls and partitions can be constructed of a suitable material capable of providing rigid support, such as PVC, CPVC, ABC, stainless steel or fiberglass. The invention is sized as needed to accommodate one or a plurality of dental operatory stations.

In an alternative embodiment, a chamber connection tube 7 is not used and there is no communication between the main chamber 6 and the output chamber 8; in addition to the vacuum output connection 9, an air vacuum output connection in the top 4 of the housing 1 connects separately with the vacuum source line 10 which in turn connects with the vacuum source. In an additional alternative embodiment, the removal of the filtered effluent from the vacuum output connection 9 is not vacuum-assisted, but drains by gravity through appropriate plumbing into a public sewer system when the internal liquid level in the output chamber 8 reaches the height of the vacuum output connection 9. The gravity-assisted filtered effluent can be further treated, if necessary, to remove soluble and suspended mercury. An additional embodiment includes the use of a drain valve at the most gravity-dependent part of the output chamber 8. In a further alternative embodiment, after particulate material containing mercury, silver and other metals has been removed from the central collection well 14 of the removable filter device 15, the removable filter device 15 can be disassembled and the filter media 19 removed, cleansed of particulate matter and debris or replaced by new filter media, replaced in the removable filter device 15, reassembled and filtering continued after screwing the removable filter device 15 onto the male-threaded hollow tube 12 on the base 13 of the housing 1. In an additional alternative embodiment, the removable filter device 15 can be enclosed by extending the housing and attaching a suitable cover to remove the filter device from view and protect it from inadvertent damage or displacement. In a further alternative embodiment, the top 4 can be slightly rounded or more dome-shaped rather than flat. In another alternative embodiment, the relative sizes of the main and output chambers can be proportionally different than that depicted in FIG. 1.

EXAMPLE 1

Using FIGS. 1, 2 and 3 to reference selected components of the invention, a preferred embodiment of the invention is described. In operation, a waste water slurry is generated during dental procedures which is removed from the patient's mouth under vacuum. The waste water slurry can contain, among other components, irrigation water and particulate material containing mercury, silver, other metals. The waste water slurry from the patient's mouth traverses the input vacuum line 2, into the input vacuum connection 3 and collects by gravity in the main chamber 6 and the central collection well 14 of the removable filter device 15. The removable filter can be custom made or any of a variety of commercially available filters that includes filter media having a pore size in the range up to 50 µm, depending on the filter selected (e.g., Series 200 to 700, Spin-on Oil Filters, System I Filtration, Tulare, Calif.; FRAM HP series filters, Allied Automotive Aftermarket, Providence, R.I.). The air component of the vacuum, meanwhile, continues to be removed from the main chamber 6, through the chamber connection tube 7, into the output chamber 8 where it combines with the filtered effluent, into the vacuum output connection 9, into the vacuum source line 10, toward the vacuum source where the air component is generally separated from the filtered effluent and released into the atmosphere while the filtered effluent is directed into a public sewer system. The vacuum in the output chamber 8 assists, in addition to gravity, in drawing the liquid slurry in the central collection well 14 of the removable filter device 15 through the perforated cylindrical wall 18 of the central collection well 14, through the filter media 19, through the perforations 20 normally arranged circularly on the base 13 of the housing 1, into the output chamber 8 where the now filtered effluent combines with the air component of the vacuum, out the vacuum output connection 9, through the vacuum source line 10 and toward the vacuum source and disposed of as previously described. During this process, larger particulate material, including mercury-containing particles and compounds, settle into the central collection well 14. Smaller particulate material entrained in the liquid is drawn by vacuum into the filter media 19 and trapped. The filtered effluent that reaches the output chamber 8 and the vacuum output connection 9 and vacuum source line 10 is substantially free of particulate mercury-containing material.

When the central collection well 14 of the removable filter device 15 has accumulated a certain amount of mercury-containing particulate material, the standing or resident fluid is removed by rotating the apparatus (approximately 45–90 degrees) from its normal vertical orientation so that the vacuum output connection 9 is rotated in an inferior direction while a vacuum is employed at this output connection 9. The removable filter device 15 is then unscrewed from the male-threaded hollow tube 12 in the flat base 13 of the housing 1. Once the removable filter device 15 is unscrewed, a filter cover with a centrally located male-threaded plug 21 is then screwed into the female-threaded filter device opening 16 thereby creating a seal with the rubber gasket ring 17 on the filter device 15. The sealed filter device retaining the particulate material containing mercury, silver and other metals can then be disposed of according to prevailing regulations or processed to reclaim the mercury and silver content of the particulate material. The female-threaded filter device opening 16 of an unused filter device 15 is then screwed onto the male-threaded hollow tube 12. To facilitate sealing, vacuum grease or equivalent can be applied to the rubber gasket ring 17 on the removable filter device 15 during filter installation. The invention is then ready to continue operation.

ADVANTAGES AND NEW FEATURES

There are several advantages of this invention. The invention is uncomplicated and simple to operate; connects with existing vacuum and drain connections typically found in a dental office; and the design is compact and easily suitable for chairside or clinic use. Except for the removable filter, the invention uses no movable parts. Aside from the vacuum source, no electrical power is required. The method and apparatus result in efficient, effective and substantial removal of mercury-containing particulate material creating a filtered effluent suitable for discharge into a public sewer system or further treatment, if necessary, for soluble and suspended mercury.

The invention includes several new features. The use of a screw-on removable filter having a central collection well component to collect larger mercury-containing particulate material and a filter media component to trap smaller particulate mercury-containing particulate material is new. Also new is the ability of the mercury-containing particulate material, whether in the central collection well or trapped in the filter media, to be easily removed from the filter. The ability of the filter to be removed, sealed and later unsealed to accomplish this purpose and allow easy storage, disposal, recycling or reclamation of the contents is also new. The use of a relative negative atmospheric pressure created by a vacuum source to operate the apparatus by drawing waste water through a main chamber, a gravity trap, a central collection well, a removable filter and an output chamber is also new. The design which permits the stated operation is also new.

Obviously, many modifications and variations of the present invention are possible in light of the above teaching. It is therefore to be understood that, within the scope of the appended claims, the invention may be practiced otherwise than as specifically described. The principles described above can be readily modified or adapted for various applications without departing from the generic concept, and therefore such adaptations and modifications are intended to be comprehended within the meaning and range of equivalents of the enclosed embodiments. It is to be understood that the terminology and phraseology herein is for the purpose of description and not of limitation.

What is claimed is:

1. An apparatus for separating insoluble particulate material from dental waste water comprising:
   a main chamber having a top, sides and a bottom, said bottom being the lowest point of said chamber with respect to the earth;

a vacuum source for placing said main chamber under vacuum;

an input line connected to the top of said main chamber for bringing dental waste water containing suspended solids to said main chamber by the vacuum created, the end of said input line being inside the main chamber;

a vacuum continuation line on one side of said main chamber having a opening to said main chamber higher with respect to the bottom of the main chamber than the end of the input line thereby causing the separation by gravity of the water and solids from gaseous components of said waste water, said continuation line connected to an output chamber located peripherally of the main chamber;

a funnel forming the bottom of said main chamber wherein the narrow end of the funnel protrudes through the bottom of said main chamber and forms a knob, said narrow end of the funnel directs said waste water through a separable connection into a central collection well of a removable filter located lower than the main and output chambers;

said central well having a wall separating said well from filter media surrounding said well;

perforations through the wall of the central well so waste water and suspended material flow into the filter media;

an exit from the filter media connected to said output chamber; and exhaust means connected to said output chamber and to said vacuum source for removing effluent from said apparatus and maintaining vacuum in said apparatus.

2. The apparatus of claim 1 wherein the removable filter is sealably mounted on the flat exterior of the main chamber by a female threaded opening in the filter for mounting on the male threaded knob of the funnel.

* * * * *